(12) United States Patent
Holoboski et al.

(10) Patent No.: US 8,193,373 B2
(45) Date of Patent: Jun. 5, 2012

(54) THERAPEUTIC COMPOUNDS

(75) Inventors: Mark Holoboski, Irvine, CA (US);
Robert M. Burk, Laguna Beach, CA (US); Mari Posner, Laguna Niguel, CA (US)

(73) Assignee: Allergan, Inc., Irvine, CA (US)

( * ) Notice: Subject to any disclaimer, the term of this patent is extended or adjusted under 35 U.S.C. 154(b) by 383 days.

(21) Appl. No.: 12/518,799

(22) PCT Filed: Dec. 4, 2007

(86) PCT No.: PCT/US2007/086326
§ 371 (c)(1),
(2), (4) Date: Nov. 12, 2009

(87) PCT Pub. No.: WO2008/073752
PCT Pub. Date: Jun. 19, 2008

(65) Prior Publication Data
US 2010/0063303 A1 Mar. 11, 2010

Related U.S. Application Data

(60) Provisional application No. 60/869,468, filed on Dec. 11, 2006.

(51) Int. Cl.
*C07D 333/16* (2006.01)
*C07C 61/06* (2006.01)
(52) U.S. Cl. .......................... 549/78; 562/503
(58) Field of Classification Search .................... 549/78; 562/503
See application file for complete search history.

(56) References Cited

U.S. PATENT DOCUMENTS

| | | | |
|---|---|---|---|
| 4,028,396 A | 6/1977 | Schaub et al. | |
| 4,141,914 A | 2/1979 | Grudzinskas et al. | |
| 4,166,452 A | 9/1979 | Generales, Jr. | |
| 4,178,461 A | 12/1979 | Schaub et al. | |
| 4,256,108 A | 3/1981 | Theeuwes | |
| 4,265,874 A | 5/1981 | Bonsen et al. | |
| 6,437,146 B1 | 8/2002 | Hattori et al. | |
| 6,710,072 B2 | 3/2004 | Burk et al. | |

FOREIGN PATENT DOCUMENTS

WO    WO 95/26729    10/1995

OTHER PUBLICATIONS

U.S. Appl. No. 60/744,236, filed Apr. 4, 2006, Y. Donde, et al.
Francis A. Carey, Organic Chemistry, New York: McGraw-Hill Book Company 1987, p. 63.
Han et. al. ,Biorganic & Medicinal Chemistry Letters 15 (2005) 3487-3490.
Remington's Pharmaceutical Sciences, Mack Publishing Company, Easton, Pa., 16th Edition, 1980.
Chourasia and Jain in J Pharm Pharmaceut Sci 6 (1): 33-66, 2003 and Shareef et. al (AAPS PharmSci 2003; 5 (2) Article 17).
Kousuke Tani; et al. "Development of a Highly Selective EP2-Receptor Agonist. Part 1: Identification of 16-hydroxy-17,17-trimethylene PGE$_2$ Derivatives"; Bioorganic & medicinal Chemistry 10 (2002) 1093-1106; Aug. 7, 2001; pp. 1093-1106.

*Primary Examiner* — Janet Andres
*Assistant Examiner* — John Mabry
(74) *Attorney, Agent, or Firm* — Kevin J. Forrestal; John E. Wurst; Doina G. Ene

(57) ABSTRACT

Compound having the formula below are disclosed herein: formula (I). Therapeutic methods, compositions, and medicaments related thereto are also disclosed.

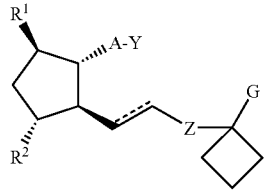

20 Claims, No Drawings

THERAPEUTIC COMPOUNDS

CROSS REFERENCE TO RELATED APPLICATIONS

This is a national stage application under 35 U.S.C. 371 of PCT patent application PCT/US2007/086326, filed on Dec. 11, 2006, which claims the benefit of U.S. Provisional Patent Application 60/869,468, filed Dec. 11, 2006, each of which is hereby incorporated by reference in its entirety.

DESCRIPTION OF THE INVENTION

Disclosed herein is a method comprising administering a compound to a mammal for the treatment of glaucoma or ocular hypertension in a mammal, wherein the compound is described herein.

Another embodiment is use of a compound in the manufacture of a medicament for the treatment of glaucoma or ocular hypertension in a mammal, wherein the compound is described herein.

Another embodiment is a composition comprising a compound described herein, wherein the composition is a liquid which is ophthalmically acceptable.

Another embodiment is a kit comprising a composition comprising a compound disclosed herein, a package for dispensing drops of the composition, and a label indicating that said composition is to be administered topically to the eye of a mammal for the treatment of glaucoma or ocular hypertension in a mammal.

The compounds are described generally by the formula

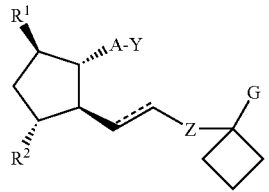

or a pharmaceutically acceptable salt, or a prodrug thereof; wherein Y is an organic acid functional group, or an amide or ester thereof comprising up to 14 carbon atoms; or Y is hydroxymethyl or an ether thereof comprising up to 14 carbon atoms; or Y is a tetrazolyl functional group;

A is —$(CH_2)_6$—, cis-$CH_2CH$=$CH$—$(CH_2)_3$—, or —$CH_2C$≡$C$—$(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein one $CH_2$ may be replaced by S or O;

$R^1$ is CN or OH;
$R^2$ is H, CN, OH, F, Cl, Br, or $CH_3$ with the proviso that if $R^1$ is OH, $R^2$ is not OH;
Z is $CH_2CHOH$, $CHOHCH_2$, or CHOH;
G is L, —$CH_2L$, OL, or SL;
L is phenyl, monocyclic heteroaryl, or $C_{1-6}$ alkyl.

A person of ordinary skill in the art understands the meaning of the stereochemistry associated with the hatched wedge/ solid wedge structural features. For example, an introductory organic chemistry textbook (Francis A. Carey, Organic Chemistry, New York: McGraw-Hill Book Company 1987, p. 63) states "a wedge indicates a bond coming from the plane of the paper toward the viewer" and the hatched wedge, indicated as a "dashed line", "represents a bond receding from the viewer."

An organic acid functional group is an acidic functional group on an organic molecule. While not intending to be limiting, organic acid functional groups may comprise an oxide of carbon, sulfur, or phosphorous. Thus, while not intending to limit the scope of the invention in any way, in certain compounds Y is a carboxylic acid, sulfonic acid, or phosphonic acid functional group.

Additionally, an amide or ester of one of the organic acids shown above comprising up to 14 carbon atoms is also contemplated. In an ester, a hydrocarbyl moiety replaces a hydrogen atom of an acid such as in a carboxylic acid ester, e.g. $CO_2Me$, $CO_2Et$, etc.

In an amide, an amine group replaces an OH of the acid. Examples of amides include $CON(R^3)_2$, $CON(OR^3)R^3$, $CON(CH_2CH_2OH)_2$, and $CONH(CH_2CH_2OH)$ where $R^3$ is independently H, $C_1$-$C_6$ alkyl, phenyl, or biphenyl. Moieties such as $CONHSO_2R^3$ are also amides of the carboxylic acid notwithstanding the fact that they may also be considered to be amides of the sulfonic acid $R^3$—$SO_3H$. The following amides are also specifically contemplated, $CONSO_2$-biphenyl, $CONSO_2$-phenyl, $CONSO_2$-heteroaryl, and $CONSO_2$-naphthyl. The biphenyl, phenyl, heteroaryl, or naphthyl may be substituted or unsubstituted.

Han et. al. (Biorganic & Medicinal Chemistry Letters 15 (2005) 3487-3490) has recently shown that the groups shown below are suitable bioisosteres for a carboxylic acid. The activity of compounds with these groups in inhibiting HCV NS3 protease was comparable to or superior to similar compounds where the group is replaced by $CO_2H$. Thus, Y could be any group depicted below.

1. Carboxylic Acid Bioisosteres According to Han et. al.

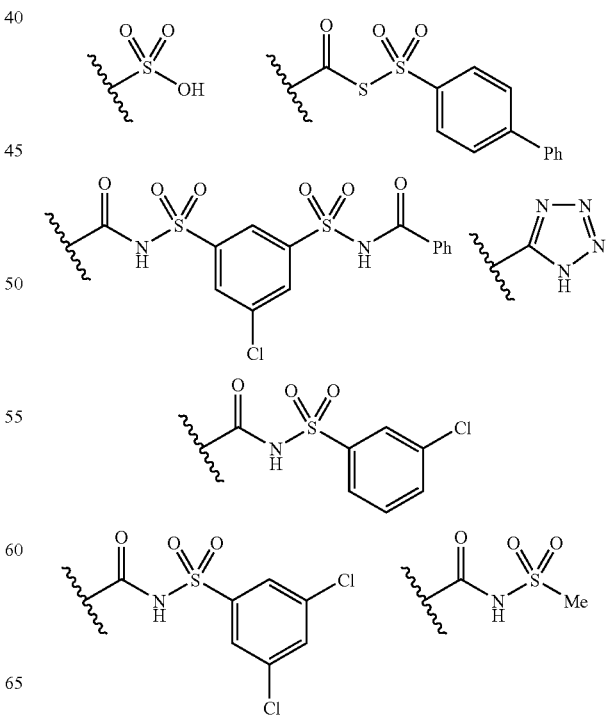

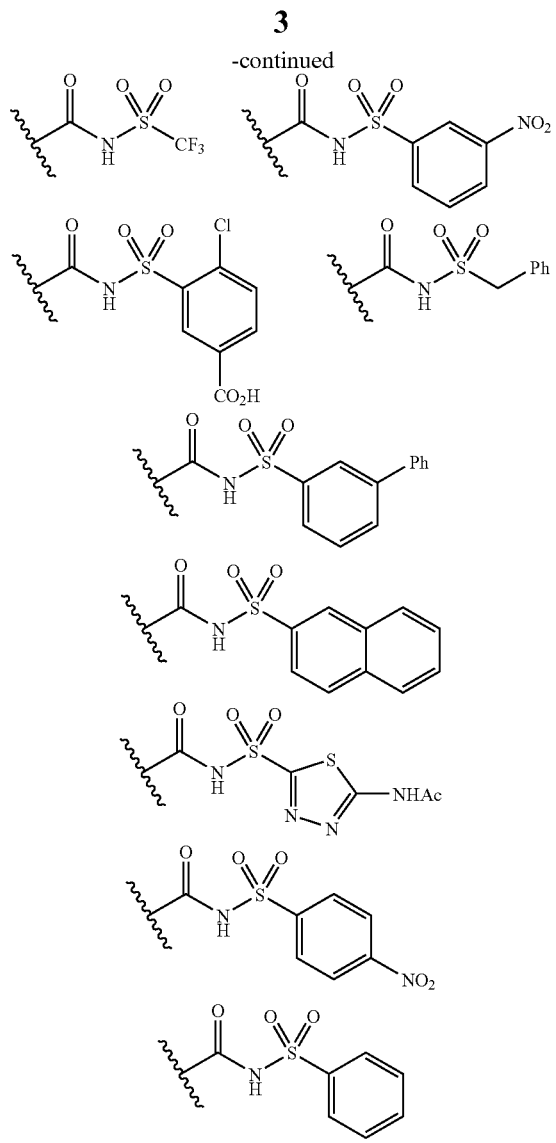

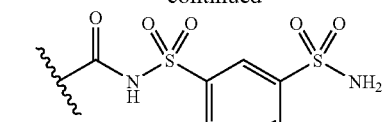

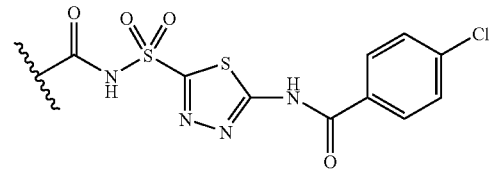

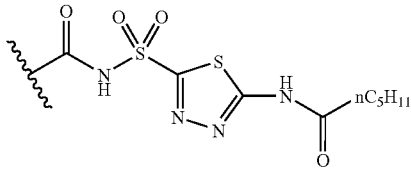

While not intending to limit the scope of the invention in any way, Y may also be hydroxymethyl or an ether thereof comprising up to 14 carbon atoms. An ether is a functional group wherein a hydrogen of an hydroxyl is replaced by carbon, e.g., Y is —$CH_2OCH_3$, —$CH_2OCH_2CH_3$, etc.

"Up to 14 carbon atoms" means that the entire Y moiety, including the carbonyl carbon of a carboxylic acid ester or amide, and both carbon atoms in the —$CH_2O$—C of an ether has 0, 1, 2, 3, 4, 5, 6, 7, 8, 9, 10, 11, 12, 13, or 14 carbon atoms.

Finally, while not intending to limit the scope of the invention in any way, Y may be a tetrazolyl functional group.

While not intending to be limiting, examples of compounds having the identified Y are depicted below. In these examples R is H or hydrocarbyl, subject to the constraints defined herein. Each structure below represents a specific embodiment which is individually contemplated, as well as pharmaceutically acceptable salts and prodrugs of compounds which are represented by the structures. However, other examples are possible which may not fall within the scope of the structures shown below.

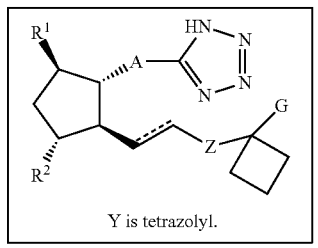

Y is tetrazolyl.

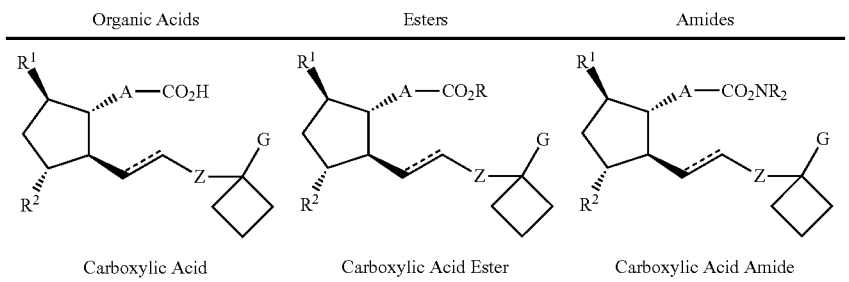

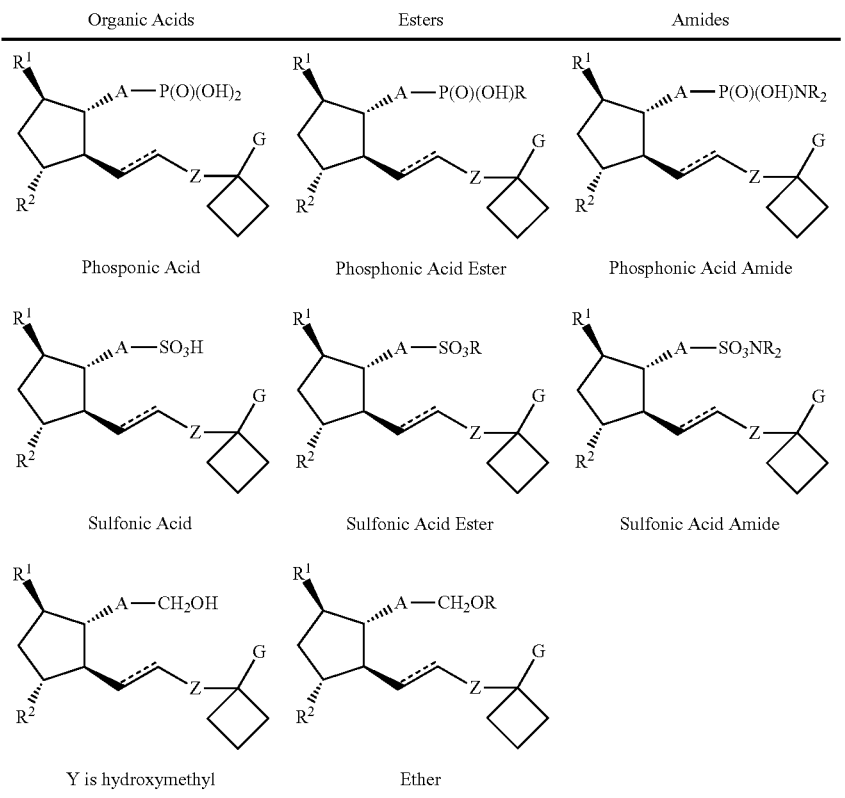

Y is tetrazolyl.

| Organic Acids | Esters | Amides |
|---|---|---|
| Phosponic Acid | Phosphonic Acid Ester | Phosphonic Acid Amide |
| Sulfonic Acid | Sulfonic Acid Ester | Sulfonic Acid Amide |
| Y is hydroxymethyl | Ether | |

An unsubstituted tetrazolyl functional group has two tautomeric forms, which can rapidly interconvert in aqueous or biological media, and are thus equivalent to one another. These tautomers are shown below.

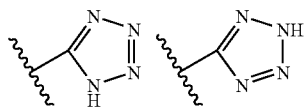

Additionally, if $R^3$ is $C_1$-$C_6$ alkyl, phenyl, or biphenyl, other isomeric forms of the tetrazolyl functional group such as the one shown below are also possible, unsubstituted and hydrocarbyl substituted tetrazolyl up to $C_{12}$ are considered to be within the scope of the term "tetrazolyl."

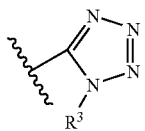

While not intending to limit the scope of the invention in any way, in one embodiment, Y is selected from the group consisting of $CO_2(R^3)$, $CON(R^3)_2$, $CON(OR^3)R^3$, $CON(CH_2CH_2OH)_2$, $CONH(CH_2CH_2OH)$, —$CH_2OH$, $P(O)(OH)_2$, $CONHSO_2R^3$, $SO_2N(R^3)_2$, $SO_2NHR^3$, and tetrazolyl-$R^3$; wherein $R^3$ is independently H, $C_1$-$C_6$ alkyl, phenyl, or biphenyl.

In relation to the identity of A disclosed in the chemical structures presented herein, A is —$(CH_2)_6$—, cis-$CH_2CH$=$CH$—$(CH_2)_3$—, or —$CH_2C$≡$C$—$(CH_2)_3$—, wherein 1 or 2 carbon atoms may be replaced with S or O; or A is —$(CH_2)_m$—Ar—$(CH_2)_o$— wherein Ar is interarylene or heterointerarylene, the sum of m and o is 1, 2, 3, or 4, and wherein one $CH_2$ may be replaced with S or O.

While not intending to be limiting, A may be —$(CH_2)_6$—, cis-$CH_2CH$=$CH$—$(CH_2)_3$—, or —$CH_2C$≡$C$—$(CH_2)_3$—.

Alternatively, A may be a group which is related to one of these three moieties in that any carbon is replaced with S and/or O. For example, while not intending to limit the scope of the invention in any way, A may be a moiety where S replaces one or two carbon atoms such as one of the following or the like.

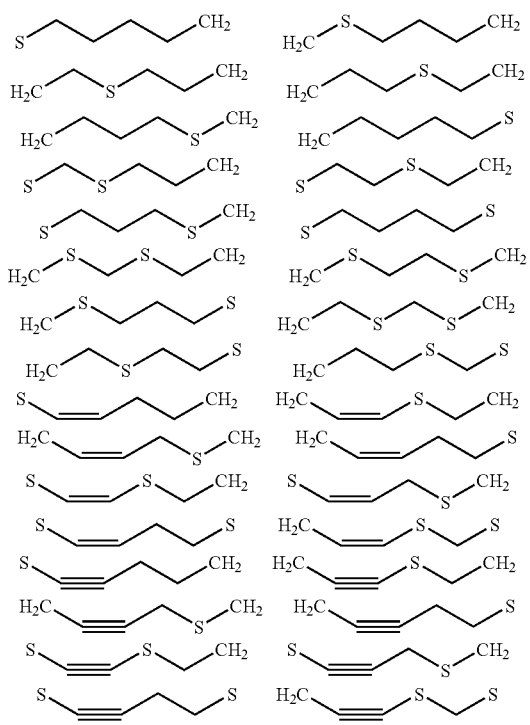

Alternatively, while not intending to limit the scope of the invention in any way, A may be a moiety where O replaces one or two carbon atoms such as one of the following or the like.

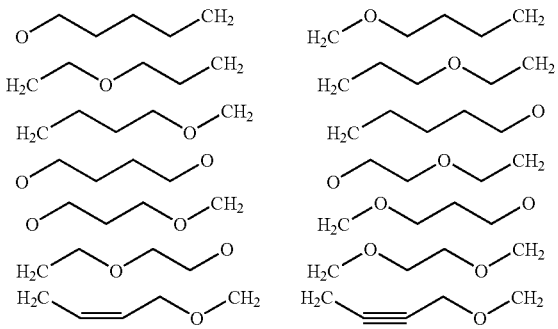

Alternatively, while not intending to limit the scope of the invention in any way, A may have an O replacing one carbon atom and an S replacing another carbon atom, such as one of the following or the like.

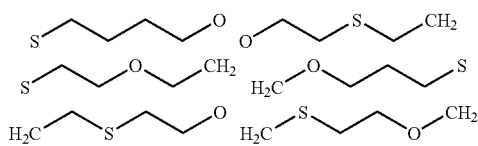

Alternatively, while not intending to limit the scope of the invention in any way, in certain embodiments A is —$(CH_2)_m$—Ar—$(CH_2)_o$— wherein Ar is interarylene or heterointerarylene, the sum of m and o is 1, 2, 3, or 4, and wherein one $CH_2$ may be replaced with S or O. In other words, while not intending to limit the scope of the invention in any way, in one embodiment A comprises 1, 2, 3, or 4 $CH_2$ moieties and Ar, e.g. —$CH_2$—Ar—, —$(CH_2)_2$—Ar—, —$CH_2$—Ar—$CH_2$—, —$CH_2$Ar—$(CH_2)_2$—, —$(CH_2)_2$—Ar—$(CH_2)_2$—, and the like;

in another embodiment A comprises O, 0, 1, 2, or 3 $CH_2$ moieties, and Ar, e.g., —O—Ar—, Ar—$CH_2$—O—, —O—Ar—$(CH_2)_2$—, —O—$CH_2$—Ar—, —O—$CH_2$—Ar—$(CH_2)_2$, and the like; or in another embodiment A comprises S, 0, 1, 2, or 3 $CH_2$ moieties, and Ar, e.g., —S—Ar—, Ar—$CH_2$—S—, —S—Ar—$(CH_2)_2$—, —S—$CH_2$—Ar—, —S—$CH_2$—Ar—$(CH_2)_2$, —$(CH_2)_2$—S—Ar, and the like.

In another embodiment, the sum of m and o is 2, 3, or 4 wherein one $CH_2$ may be replaced with S or O.

In another embodiment, the sum of m and o is 3 wherein one $CH_2$ may be replaced with S or O.

In another embodiment, the sum of m and o is 2 wherein one $CH_2$ may be replaced with S or O.

In another embodiment, the sum of m and o is 4 wherein one $CH_2$ may be replaced with S or O.

Interarylene or heterointerarylene refers to an aryl ring or ring system or a heteroaryl ring or ring system which connects two other parts of a molecule, i.e. the two parts are bonded to the ring in two distinct ring positions. Interarylene or heterointerarylene may be substituted or unsubstituted. Unsubstituted interarylene or heterointerarylene has no substituents other than the two parts of the molecule it connects. Substituted interarylene or heterointerarylene has substituents in addition to the two parts of the molecule it connects.

In one embodiment, Ar is substituted or unsubstituted interphenylene, interthienylene, interfurylene, interpyridinylene, interoxazolylene, and interthiazolylene. In another embodiment Ar is interphenylene (Ph). In another embodiment A is —$(CH_2)_2$-Ph-. Substituents may have 4 or less heavy atoms, wherein the heavy atoms are C, N, O, S, P, F, Cl, Br, and/or I in any stable combination. Any number of hydrogen atoms required for a particular substituent will also be included. A substituent must be stable enough for the compound to be useful as described herein. In addition to the atoms listed above, a substituent may also have a metal cation or any other stable cation having an atom not listed above if the substituent is acidic and the salt form is stable. For example, —OH may form an —$O^-Na^+$ salt or $CO_2H$ may form a $CO_2^-K^+$ salt. Any cation of the salt is not counted in the "4 or less heavy atoms." Thus, the substituent may be hydrocarbyl having up to 4 carbon atoms, including alkyl up to $C_4$, alkenyl, alkynyl, and the like;

hydrocarbyloxy up to $C_3$;

organic acid such as $CO_2H$, $SO_3H$, $P(O)(OH)_2$, and the like, and salts thereof;

$CF_3$;

halo, such as F, Cl, or Br;

hydroxyl;

$NH_2$ and alkylamine functional groups up to $C_3$;

other N or S containing substituents such as CN, $NO_2$, and the like;

and the like.

In one embodiment A is —$(CH_2)_m$—Ar—$(CH_2)_o$— wherein Ar is interphenylene, the sum of m and o is 1, 2, or 3, and wherein one $CH_2$ may be replaced with S or O.

In another embodiment A is —$CH_2$—Ar—$OCH_2$—. In another embodiment A is —$CH_2$—Ar—$OCH_2$— and Ar is interphenylene. In another embodiment, Ar is attached at the 1 and 3 positions, otherwise known as m-interphenylene, such as when A has the structure shown below.

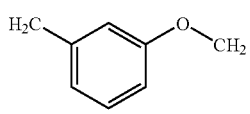

In another embodiment A is —(CH$_2$)$_6$—, cis-CH$_2$CH═CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph- wherein one CH$_2$ may be replaced with S or O.

In another embodiment A is —(CH$_2$)$_6$—, cis-CH$_2$CH═CH—(CH$_2$)$_3$—, or —CH$_2$C≡C—(CH$_2$)$_3$—, wherein 1 or 2 carbon atoms may be replaced with S or O; or A is —(CH$_2$)$_2$-Ph-.

In other embodiments, A has one of the following structures, where Y is attached to the aromatic or heteroaromatic ring.

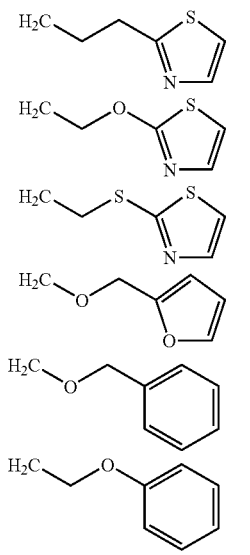

In another embodiment A is —CH$_2$OCH$_2$Ar.
In another embodiment A is —CH$_2$SCH$_2$Ar.
In another embodiment A is —(CH$_2$)$_3$Ar.
In another embodiment A is —CH$_2$—O—(CH$_2$)$_4$—.
In another embodiment A is —CH$_2$S(CH$_2$)$_4$—.
In another embodiment A is —(CH$_2$)$_6$—.
In another embodiment A is cis-CH$_2$CH═CH—(CH$_2$)$_3$—.
In another embodiment A is —CH$_2$C≡C—(CH$_2$)$_3$—.
In another embodiment A is —S(CH$_2$)$_3$S(CH$_2$)$_2$—.
In another embodiment A is —(CH$_2$)$_4$OCH$_2$—.
In another embodiment A is cis-CH$_2$CH═CH—CH$_2$OCH$_2$—.
In another embodiment A is —CH$_2$CH≡CH—CH$_2$OCH$_2$—.
In another embodiment A is —(CH$_2$)$_2$S(CH$_2$)$_3$—.
In another embodiment A is —CH$_2$-Ph-OCH$_2$—, wherein Ph is interphenylene.
In another embodiment A is —CH$_2$-mPh-OCH$_2$—, wherein mPh is m-interphenylene.
In another embodiment A is —CH$_2$—O—(CH$_2$)$_4$—.
In another embodiment A is —CH$_2$—O—CH$_2$—Ar—, wherein Ar is 2,5-interthienylene.
In another embodiment A is —CH$_2$—O—CH$_2$—Ar—, wherein Ar is 2,5-interfurylene.

Compounds according to the each of the structures depicted below, and pharmaceutically acceptable salts thereof, and prodrugs thereof, are contemplated as individual embodiments. In other words, each structure represents a different embodiment.

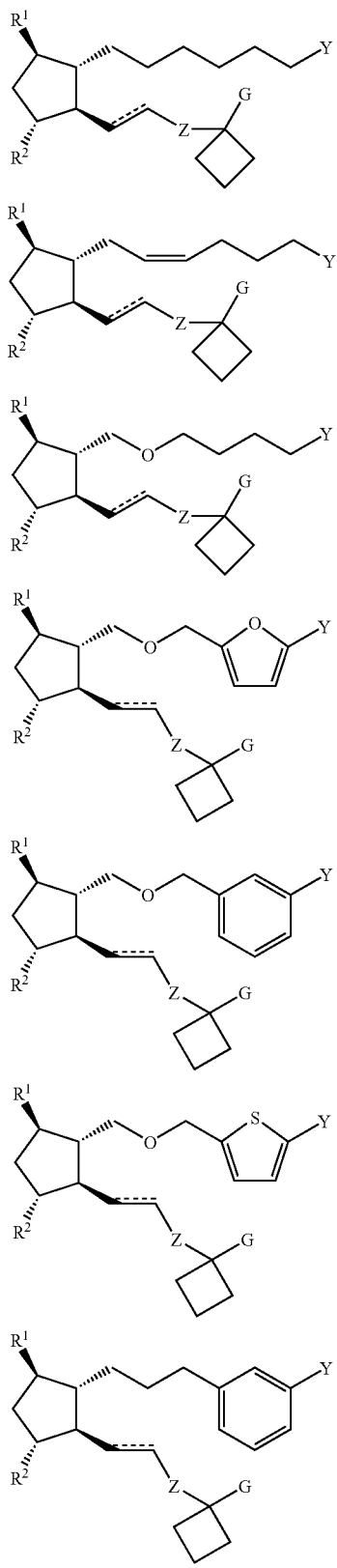

-continued

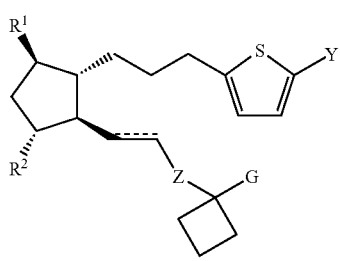

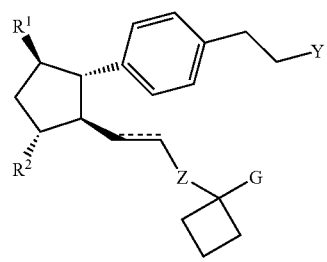

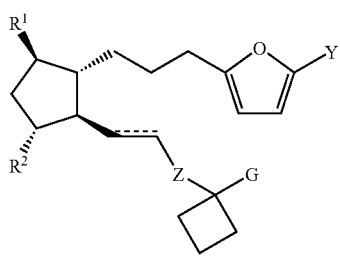

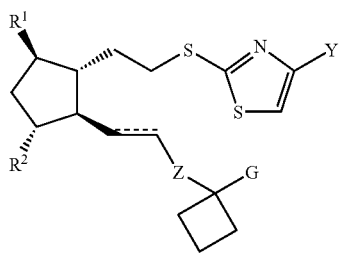

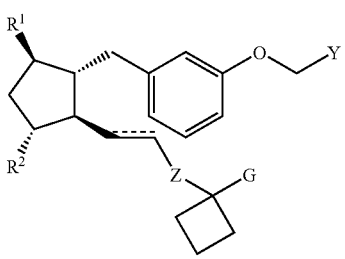

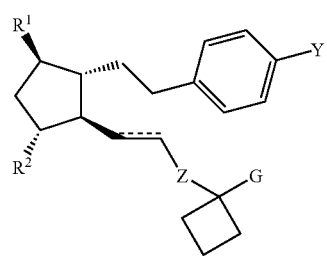

-continued

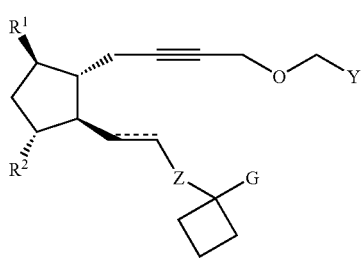

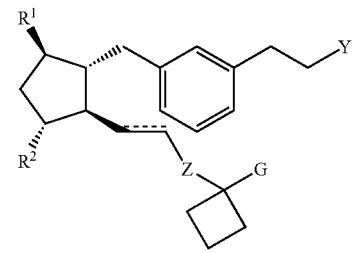

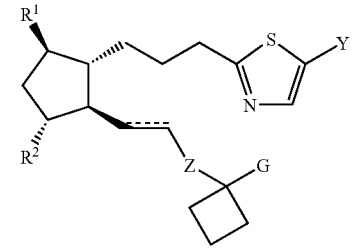

$R^1$ is CN or OH. Thus, compounds according to the each of the structures depicted below, and pharmaceutically acceptable salts thereof, and prodrugs thereof, are contemplated as individual embodiments. In other words, each structure represents a different embodiment.

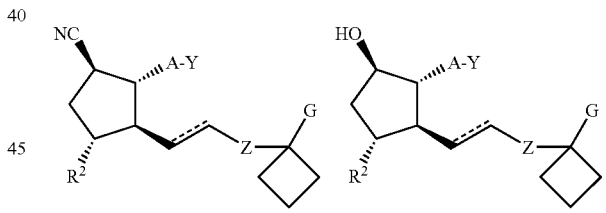

$R^2$ is H, CN, OH, F, Cl, Br, or $CH_3$ with the proviso that if is OH, $R^2$ is not OH. Thus, compounds according to the each of the structures depicted below, and pharmaceutically acceptable salts thereof, and prodrugs thereof, are contemplated as individual embodiments. In other words, each structure represents a different embodiment.

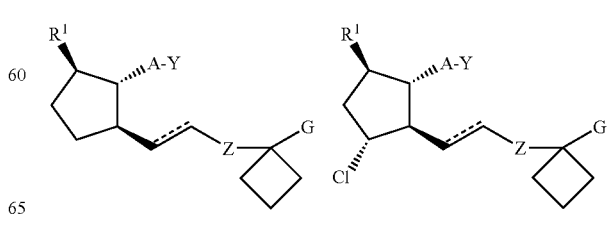

-continued

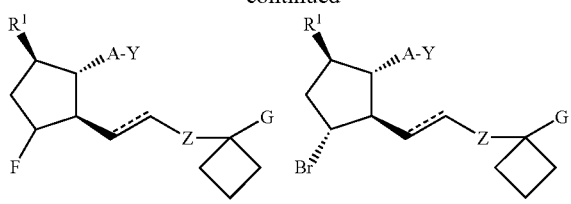

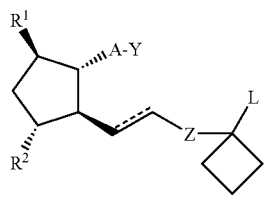

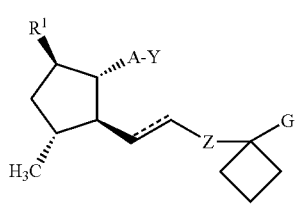

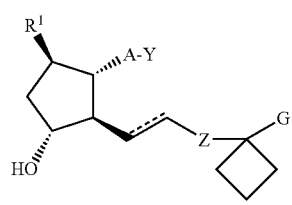

Z is —CH$_2$CHOH, CHOHCH$_2$, or CHOH. Thus, compounds according to the each of the structures depicted below, and pharmaceutically acceptable salts thereof, and prodrugs thereof, are contemplated as individual embodiments. In other words, each structure represents a different embodiment.

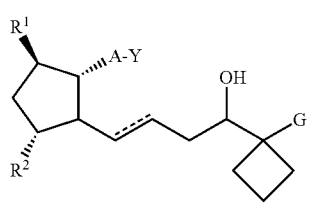

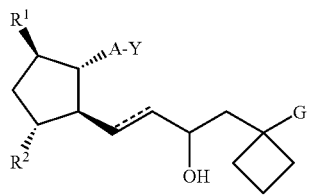

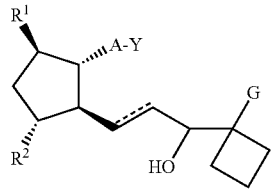

G is L, —CH$_2$L, OL, or SL. Thus, compounds according to the each of the structures depicted below, and pharmaceutically acceptable salts thereof, and prodrugs thereof, are contemplated as individual embodiments. In other words, each structure represents a different embodiment.

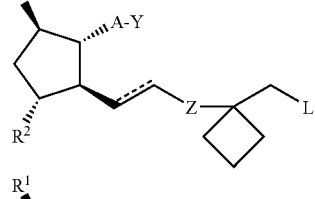

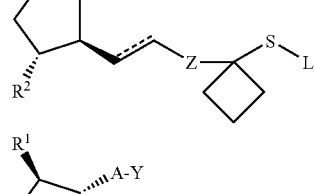

L is phenyl or monocyclic heteroaryl, or C$_{1-6}$ alkyl. Phenyl or monocyclic heteroaryl may be substituted or unsubstituted. If L is substituted, it has 1, 2, 3, or 4 heavy atoms, wherein the heavy atoms are C, N, O, S, P, F, Cl, Br, and/or I in any stable combination. That is, the possible substituents on phenyl or heterocyclic aryl are the same as those on interarylene or interheteroarylene, and like interarylene and heterointerarylene, the substituents may be the same or different with respect to one another. Likewise, the substituents on Ar and L may be the same or different with respect to one another. In particular phenyl, thienyl, furyl, and pyridinyl, either substituted or unsubstituted, are contemplated.

C$_{1-6}$ alkyl is alkyl having 1, 2, 3, 4, 5, or 6 carbon atoms. Alkyl is a moiety having only carbon and hydrogen and no double bonds. In one embodiment G, is ethyl.

Composition Example

A composition comprising a compound according to any structure disclosed herein, wherein the composition is a liquid which is ophthalmically acceptable.

Kit Example

Another embodiment is a kit comprising a composition comprising a compound according to any structure disclosed herein, a package for dispensing drops of the composition, and a label indicating that said composition is to be administered topically to the eye of a mammal for the treatment of glaucoma or ocular hypertension in a mammal.

Method Example

A method comprising administering a compound according to any structure disclosed herein to a mammal for the treatment of glaucoma or ocular hypertension in a mammal.

Medicament Examples

Use of a compound according to any structure disclosed herein in the manufacture of a medicament for the treatment of glaucoma or ocular hypertension in a mammal.

A medicament comprising a compound according to any structure disclosed herein for the treatment of glaucoma or ocular hypertension in a mammal.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds may be in the range of about 0.5 or about 1 to about 100 mg/kg/day.

A liquid which ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
|---|---|
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

The compounds disclosed herein are also useful in combination with other drugs useful for the treatment of glaucoma or other conditions.

For the treatment of glaucoma, combination treatment with the following classes of drugs are contemplated:

β-Blockers (or β-adrenergic antagonists) including carteolol, levobunolol, metipranolol, timolol hemihydrate, timolol maleate, β1-selective antagonists such as betaxolol, and the like, or pharmaceutically acceptable salts or prodrugs thereof;

Adrenergic Agonists including
non-selective adrenergic agonists such as epinephrine borate, epinephrine hydrochloride, and dipivefrin, and the like, or pharmaceutically acceptable salts or prodrugs thereof; and
$\alpha_2$-selective adrenergic agonists such as apraclonidine, brimonidine, and the like, or pharmaceutically acceptable salts or prodrugs thereof;

Carbonic Anhydrase Inhibitors including acetazolamide, dichlorphenamide, methazolamide, brinzolamide, dorzolamide, and the like, or pharmaceutically acceptable salts or prodrugs thereof;

Cholinergic Agonists including
direct acting cholinergic agonists such as carbachol, pilocarpine hydrochloride, pilocarbine nitrate, pilocarpine, and the like, or pharmaceutically acceptable salts or prodrugs thereof;
chlolinesterase inhibitors such as demecarium, echothiophate, physostigmine, and the like, or pharmaceutically acceptable salts or prodrugs thereof;
Glutamate Antagonists and other neuroprotective agents such as $Ca^{2+}$ channel blockers such as memantine, amantadine, rimantadine, nitroglycerin, dextrophan, dextromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, barnidipine, verapamil, lidoflazine, prenylamine lactate, amiloride, and the like, or pharmaceutically acceptable salts or prodrugs thereof;
Prostamides such as bimatoprost, or pharmaceutically acceptable salts or prodrugs thereof; and
Prostaglandins including travoprost, UFO-21, chloprostenol, fluprostenol, 13,14-dihydro-chloprostenol, isopropyl unoprostone, latanoprost and the like.
Cannabinoids including CB1 agonists such as WIN-55212-2 and CP-55940 and the like, or pharmaceutically acceptable salts or prodrugs thereof.

For treatment of diseases affecting the eye including glaucoma, these compounds can be administered topically, periocularly, intraocularly, or by any other effective means known in the art.

In addition to the treatment of glaucoma, prostaglandin $EP_2$ selective agonists are believed to have several medical uses. For example, U.S. Pat. No. 6,437,146 teaches the use of prostaglandin $EP_2$ selective agonists "for treating or preventing inflammation and pain in joint and muscle (e.g., rheumatoid arthritis, rheumatoid spondylitis, osteoarthritis, gouty arthritis, juvenile arthritis, etc.), inflammatory skin condition (e.g., sunburn, burns, eczema, dermatitis, etc.), inflammatory eye condition (e.g., conjunctivitis, etc.), lung disorder in which inflammation is involved (e.g., asthma, bronchitis, pigeon fancier's disease, farmer's lung, etc.), condition of the gastrointestinal tract associated with inflammation (e.g., aphthous ulcer, Chrohn's disease, atrophic gastritis, gastritis varialoforme, ulcerative colitis, coeliac disease, regional ileitis, irritable bowel syndrome, etc.), gingivitis, inflammation, pain and tumescence after operation or injury, pyrexia, pain and other conditions associated with inflammation, allergic disease, systemic lupus crythematosus, scleroderma, polymyositis, tendinitis, bursitis, periarteritis nodose, rheumatic fever, Sjgren's syndrome, Behcet disease, thyroiditis, type I diabetes, diabetic complication (diabetic microangiopathy, diabetic retinopathy, diabetic neohropathy, etc.), nephrotic syndrome, aplastic anemia, myasthenia gravis, uveitis contact dermatitis, psoriasis, Kawasaki disease, sarcoidosis, Hodgkin's disease, Alzheimers disease, kidney dysfunction (nephritis, nephritic syndrome, etc.), liver dysfunction (hepatitis, cirrhosis, etc.), gastrointestinal dysfunction (diarrhea, inflammatory bowel disease, etc.) shock, bone disease characterized by abnormal bone metabolism such as osteoporosis (especially, postmenopausal osteoporosis), hypercalcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cachexia, calculosis, lithiasis (especially, urolithiasis), solid carcinoma, mesangial proliferative glomerulonephritis, edema (e.g. cardiac edema, cerebral edema, etc.), hypertension such as malignant hypertension or the like, premenstrual tension, urinary calculus, oliguria such as the one caused by acute or chronic failure, hyperphosphaturia, or the like."

U.S. Pat. No. 6,710,072 teaches the use of $EP_2$ agonists for the treatment or prevention of "osteoporosis, constipation, renal disorders, sexual dysfunction, baldness, diabetes, cancer and in disorder of immune regulation . . . various pathophysiological diseases including acute myocardial infarction, vascular thrombosis, hypertension, pulmonary hypertension, ischemic heart disease, congestive heart failure, and angina pectoris."

These compounds can also be used to treat or prevent conditions affecting the posterior part of the eye include maculopathies/retinal degeneration such as non-exudative age related macular degeneration (ARMD), exudative age related macular degeneration (ARMD), choroidal neovascularization, diabetic retinopathy, acute macular neuroretinopathy, central serous chorioretinopathy, cystoid macular edema, and diabetic macular edema; uveitis/retinitis/choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vascular diseases/exudative diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis. Preferably, the disease or condition is retinitis pigmentosa, proliferative vitreal retinopathy (PVR), age-related macular degeneration (ARMD), diabetic retinopathy, diabetic macular edema, retinal detachment, retinal tear, uveitus, or cytomegalovirus retinitis.

These compounds are also useful in treating asthma.

Synthetic Methods

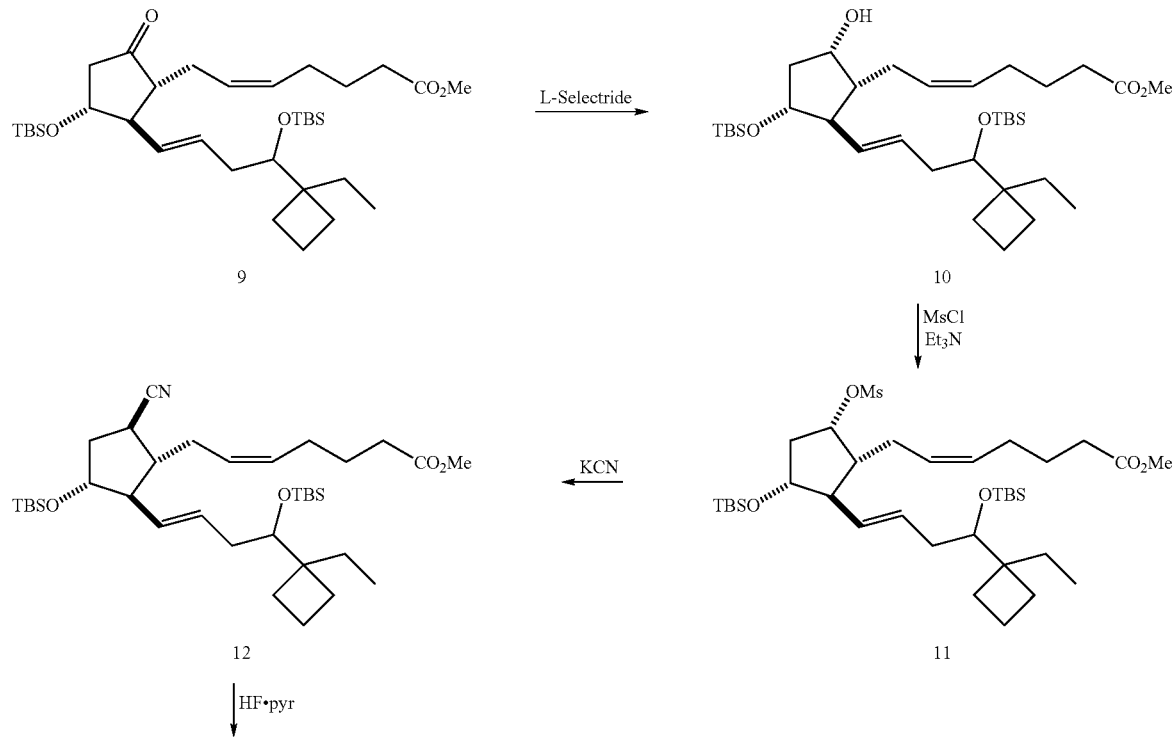

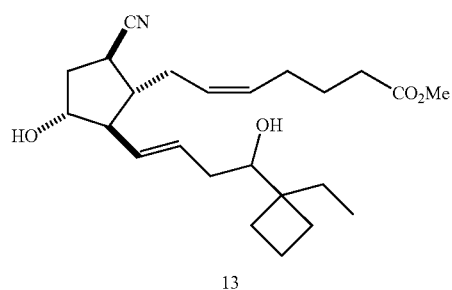

13

LiOH →

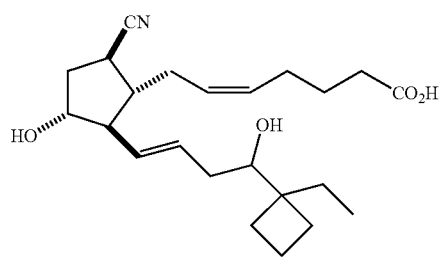

1H

↓ H₂, Pd/C

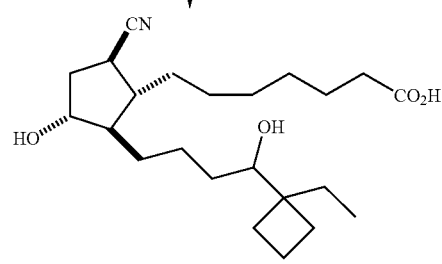

2H

Example 9

(Z)-methyl 7-((1R,2R,3R)-3-(tert-butyldimethylsilyloxy)-2-((E)-4-(tert-butyldimethylsilyloxy)-4-(1-ethylcyclobutyl)but-1-enyl)-5-oxocyclopentyl)hept-5-enoate For the preparation of Methyl Ester (9), see Kousuke, T. et al. *Bioorg. Med. Chem.* 2002, 10, 1093.

Example 10

(Z)-methyl 7-((1R,2R,3R,5S)-3-(tert-butyldimethylsilyloxy)-2-((E)-4-(tert-butyldimethylsilyloxy)-4-(1-ethylcyclobutyl)but-1-enyl)-5-hydroxycyclopentyl)hept-5-enoate L-Selectride (1.2 mL, 1.2 mmol; 1M THF) was added to a solution of Ester (9) (540 mg, 0.869 mmol) in THF (15 mL)@−78° C. After having stirred 30 min at this temperature, 3% $H_2O_2$ (27 mL) was added slowly and the reaction was warmed to room temperature and allowed to stir 60 min. $NH_4Cl$ (sat.) was added, and the mixture was extracted with EtOAC (3×). The combined organics were washed with brine, dried ($Na_2SO_4$) and concentrated. Hash Column Chromatography (FCC) 19:1 to 8:1 hexanes/EtOAc, gave 447 mg of Alcohol (10).

Example 11

(Z)-methyl 7-((1R,2R,3R,5S)-3-(tert-butyldimethylsilyloxy)-2-((E)-4-(tert-butyldimethylsilyloxy)-4-(1-ethylcyclobutyl)but-1-enyl)-5-(methylsulfonyloxy)cyclopentyl)hept-5-enoate MsCl (0.135 mL, 1.72 mmol) was added to a mixture of Alcohol (10) (447 mg, 0.717 mmol) and $Et_3N$ (217 mg, 2.15 mmol) in —$CH_2Cl_2$ (5 mL) at rt. After 16 h, the mixture was quenched with $NaHCO_3$, extracted with —$CH_2Cl_2$ (2×) and hexanes (1×). The combined organics were washed with brine, dried ($Na_2SO_4$), and concentrated. FCC 8:1 to 5:1 hexanes/EtOAc gave 372 mg of Mesylate (11).

Example 12

(Z)-methyl 7-((1S,2R,3R,5R)-3-(tert-butyldimethylsilyloxy)-2-((E)-4-(tert-butyldimethylsilyloxy)-4-(1-ethylcyclobutyl)but-1-enyl)-5-cyanocyclopentyl)hept-5-enoate KCN (105 mg, 1.62 mmol) was added to a solution of Mesylate (11) (372 mg, 0.54 mmol) in DMSO (6 mL), and the reaction was heated to 65° C. for 16 h. The mixture was diluted with water and brine, extracted with $CHCl_3$ (5×) and the combined organics were washed with water, dried ($Na_2SO_4$), and concentrated. FCC 9.5:0.5 hexanes/EtOAc gave 68 mg of Nitrile (12).

Example 13

(Z)-methyl 7-((1S,2R,3R,5R)-5-cyano-2-((E)-4-(1-ethylcyclobutyl)-4-hydroxybut-1-enyl)-3-hydroxycyclopentyl)hept-5-enoate HF pyr (0.3 mL) was added to a solution of Nitrile (12) in MeCN (2 mL). After 3 h, the mixture was quenched with $NaHCO_3$, extracted with EtOAc (3×), and the combined organics were washed with brine, dried ($Na_2SO_4$), and concentrated. FCC 2:1 to 1:1 to 2:3 hexanes/EtOAc gave 8 mg of Diol (13) as a mixture of two C(16) diastereomers.

Example 1H (Z)-7-((1S,2R,3R,5R)-5-cyano-2-((E)-4-(1-ethylcyclobutyl)-4-hydroxybut-1-enyl)-3-hydroxycyclopentyl)hept-5-enoic acid To the faster moving isomer of Diol (13) (4 mg, 0.0099 mmol) in THF (1 mL) was added a solution of 0.5 N LiOH (1 mL). After 16 h, the mixture was purified by FCC 100% EtOAc to give 1.2 mg of Acid (1H).
Example 1L
(Z)-7-((1S,2R,3R,5R)-5-cyano-2-((E)-4-(1-ethylcyclobutyl)-4-hydroxybut-1-enyl)-3-hydroxycyclopentyl)hept-5-enoic acid
The slower moving diasteromer of Example 13 was reacted in accordance with the process of Example 1H to yield the above named compound.
1H
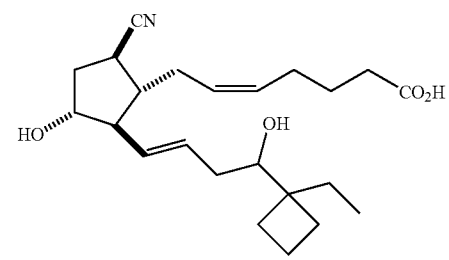
1L
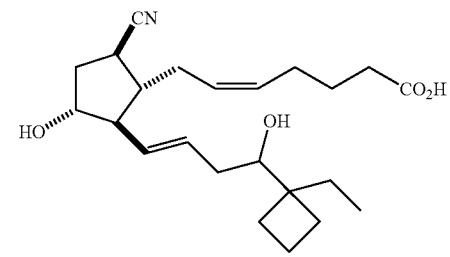
2H
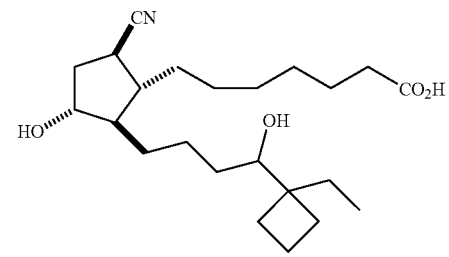
2L
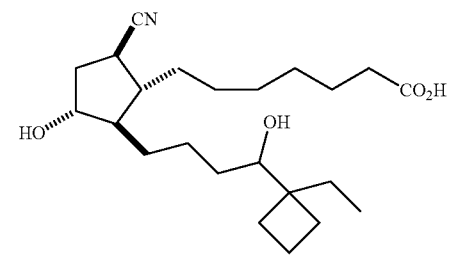
3H
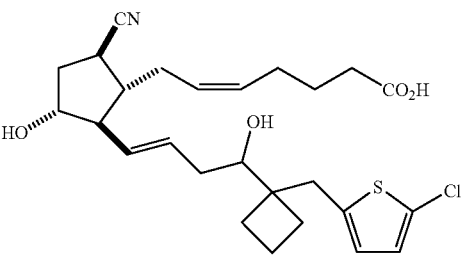
3L
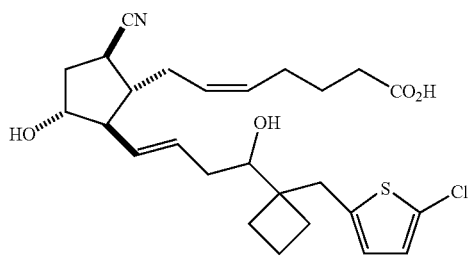
4H
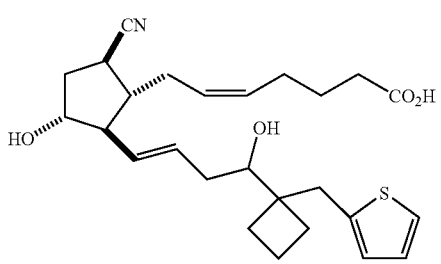
4L
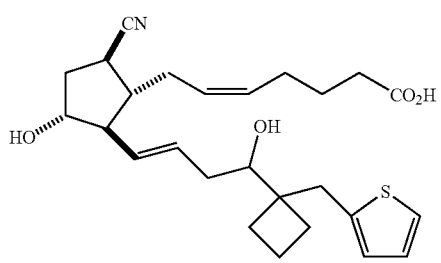
23
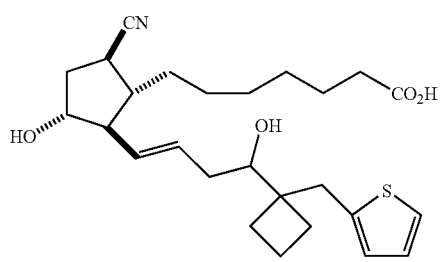
24
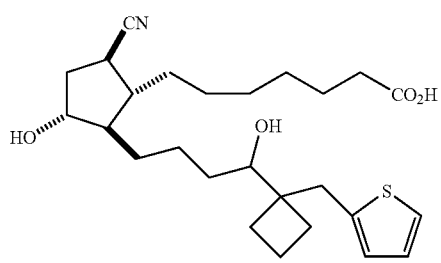
7H
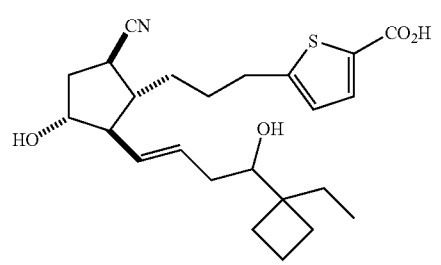

-continued

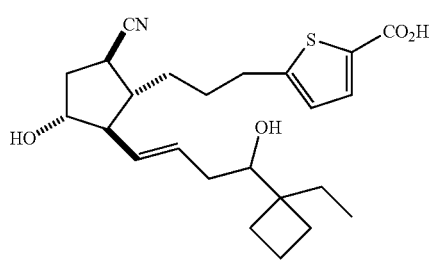

7L

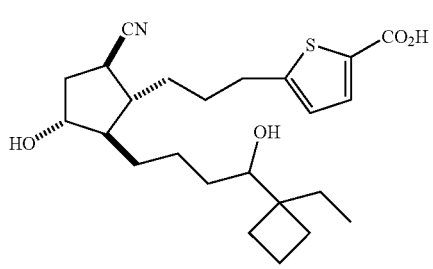

8H

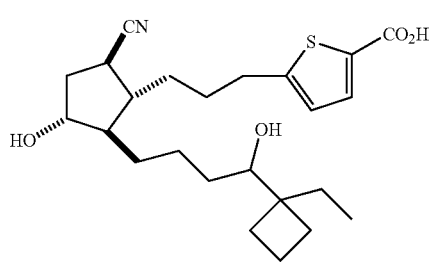

8L

Example 2H 7-((1S,2R,3R,5R)-5-cyano-2-(4-(1-ethylcyclobutyl)-4-hydroxybutyl)-3-hydroxycyclopentyl)heptanoic acid Pd—C (4 mg) was added to a solution of Acid (1H) (4 mg, 0.01 mmol) in MeOH (2 mL) and the reaction was stirred under an atmosphere of $H_2$ for 16 h. The mixture was concentrated and FCC 100% EtOAc to 9:1 EtOAc/MeOH provided 3.1 mg of Acid (2H).

Example 2L 7-((1S,2R,3R,5R)-5-cyano-2-(4-(1-ethylcyclobutyl)-4-hydroxybutyl)-3-hydroxycyclopentyl)heptanoic acid The compound obtained via Example 1L was reacted in accordance with the process of Example 2H to yield the above named compound.

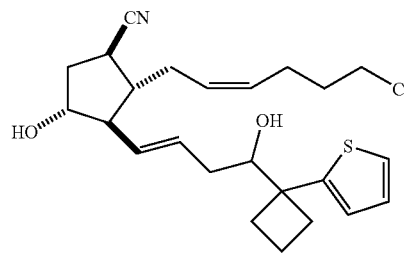

4H

-continued

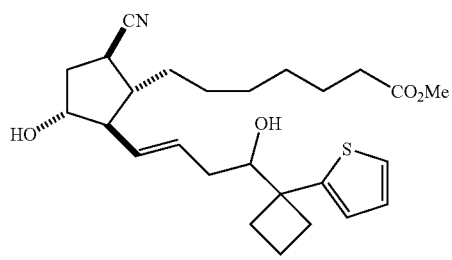

5

↓ LiOH

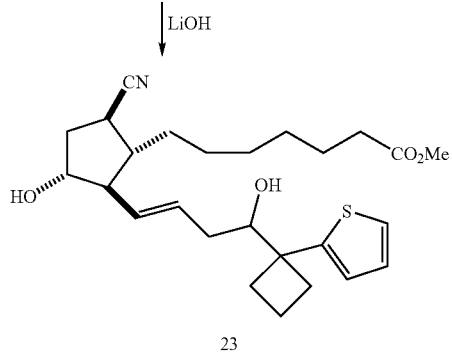

23

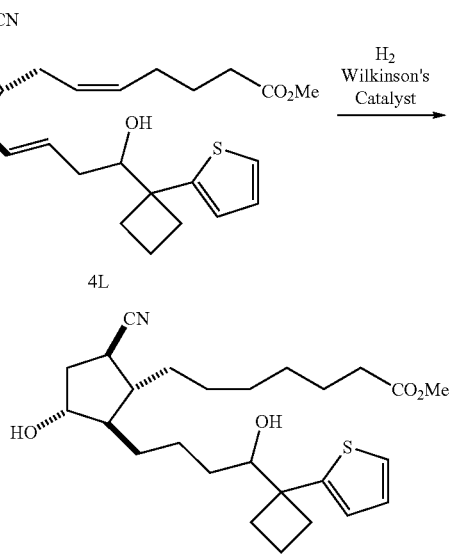

4L

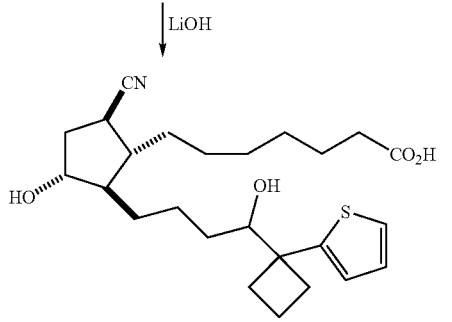

6

↓ LiOH

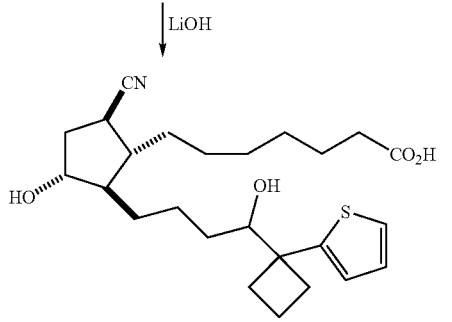

24

Example 4H (Z)-methyl 7-((1S,2R,3R,5R)-5-cyano-3-hydroxy-2-((E)-4-hydroxy-4-(1-(thiophen-2-yl)cyclobutyl)but-1-enyl)cyclopentyl)hept-5-enoate Substituting Vinyl Iodide (21) for Vinyl Iodide (15), the processes described in Examples 9-13 were used to yield the above named compound.

Example 4L (Z)-methyl 7-((1S,2R,3R,5R)-5-cyano-3-hydroxy-2-((E)-4-hydroxy-4-(1-(thiophen-2-yl)cyclobutyl)but-1-enyl)cyclopentyl)hept-5-enoate Substituting Vinyl Iodide (21) for Vinyl Iodide (15), the processes described in Examples 9-13 were used to yield the above named compound.

Example 5 methyl 7-((1S,2R,3R,5R)-5-cyano-3-hydroxy-2-((E)-4-hydroxy-4-(1-(thiophen-2-yl)cyclobutyl)but-1-enyl)cyclopentyl)heptanoate Wilkinson's Catalyst (5 mg, 0.0055 mmol) was added to a solution of Ester (4H) in EtOH (5 mL). The reaction stirred under an atmosphere of $H_2$ for 16 h, was concentrated, and FCC 1:1 hexanes/EtOAc provided 2.6 mg of Ester (5).

Example 6 methyl 7-((1S,2R,3R,5R)-5-cyano-3-hydroxy-2-(4-hydroxy-4-(1-(thiophen-2-yl)cyclobutyl)butyl)cyclopentyl)heptanoate Wilkinson's Catalyst (5 mg, 0.0055 mmol) was added to a solution of Ester (4H) in EtOH (5 mL). The reaction stirred under an atmosphere of $H_2$ for 16 h, was concentrated, and FCC 1:1 hexanes/EtOAc provided 2.6 mg of Ester (6).

Example 23

7-((1S,2R,3R,5R)-5-cyano-3-hydroxy-2-((E)-4-hydroxy-4-(1-(thiophen-2-yl)cyclobutyl)but-1-enyl)cyclopentyl)heptanoic acid The compound obtained via Example 5 was reacted in accordance with the process of Example 1H to yield the above named compound.

Example 24

7-((1S,2R,3R,5R)-5-cyano-3-hydroxy-2-(4-hydroxy-4-(1-(thiophen-2-yl)cyclobutyl)butyl)cyclopentyl) heptanoic acid The compound obtained via Example 6 was reacted in accordance with the process of Example 1H to yield the above named compound.

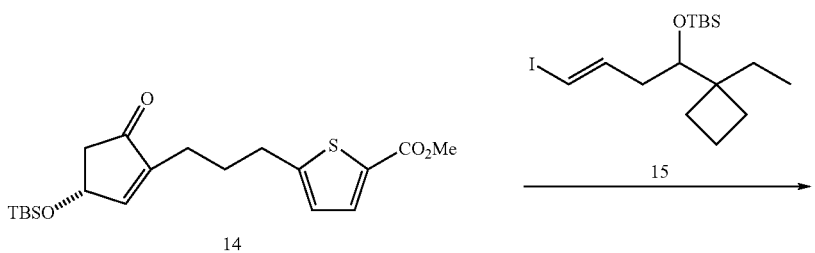

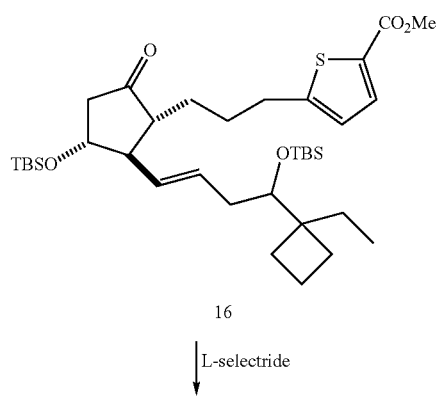

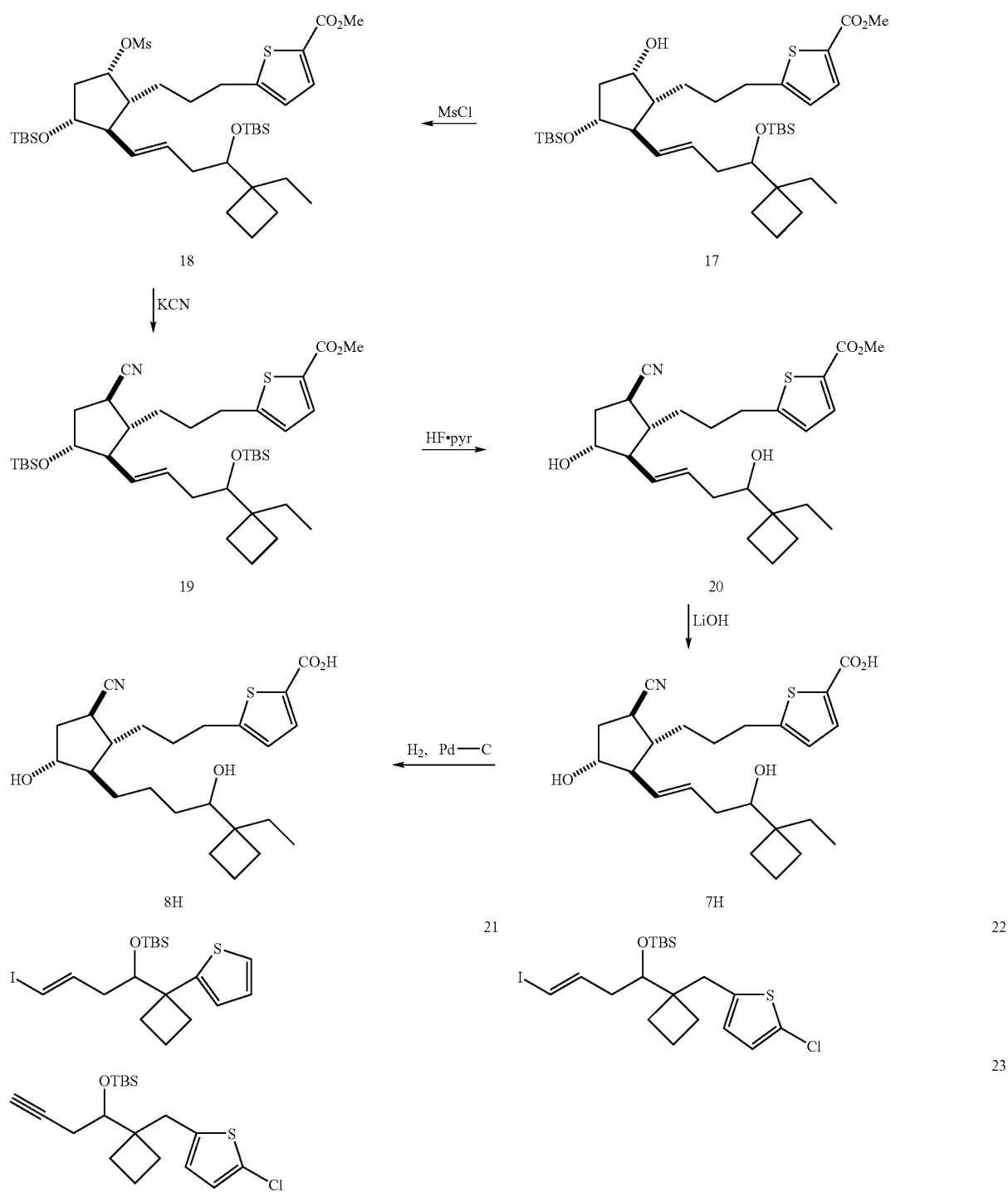

Example 14

(R)-methyl 5-(3-(3-(tert-butyldimethylsilyloxy)-5-oxocyclopent-1-enyl)propyl)thiophene-2-carboxylate This compound was prepared as described in U.S. Provisional Patent Application No. 60/744,236 filed on Apr. 4, 2006, which is incorporated by reference herein.

Example 15

(E)-tert-butyl(1-(1-ethylcyclobutyl)-4-iodobut-3-enyloxy)dimethylsilane

For the preparation of Vinyl Iodide (15), see Kousuke, T. et al. *Bioorg. Med. Chem.* 2002, 10, 1093.

Example 16 methyl 5-(3-((1R,2R,3R)-3-(tert-butyldimethylsilyloxy)-2-((E)-4-(tert-butyldimethylsilyloxy)-4-(1-ethylcyclobutyl)but-1-enyl)-5-oxocyclopentyl)propyl)thiophene-2-carboxylate The compound obtained via Example 14 was reacted in accordance with the process of Example 9 to yield the above named compound.

Example 17 methyl 5-(3-((1R,2R,3R,5S)-3-(tert-butyldimethylsilyloxy)-2-((E)-4-(tert-butyldimethylsilyloxy)-4-(1-ethylcyclobutyl)but-1-enyl)-5-hydroxycyclopentyl)propyl)thiophene-2-carboxylate The compound obtained via Example 16 was reacted in accordance with the process of Example 10 to yield the above named compound.

Example 18 methyl 5-(3-((1R,2R,3R,5S)-3-(tert-butyldimethylsilyloxy)-2-((E)-4-(tert-butyldimethylsilyloxy)-4-(1-ethylcyclobutyl)but-1-enyl)-5-(methylsulfonyloxy)cyclopentyl)propyl)thiophene-2-carboxylate The compound obtained via Example 17 was reacted in accordance with the process of Example 11 to yield the above named compound.

Example 19 methyl 5-(3-((1S,2R,3R,5R)-3-(tert-butyldimethylsilyloxy)-2-((E)-4-(tert-butyldimethylsilyloxy)-4-(1-ethylcyclobutyl)but-1-enyl)-5-cyanocyclopentyl)propyl)thiophene-2-carboxylate The compound obtained via Example 18 was reacted in accordance with the process of Example 12 to yield the above named compound.

Example 20 methyl 5-(3-((1S,2R,3R,5R)-5-cyano-2-((E)-4-(1-ethylcyclobutyl)-4-hydroxybut-1-enyl)-3-hydroxycyclopentyl)propyl)thiophene-2-carboxylate The compound obtained via Example 19 was reacted in accordance with the process of Example 13 to yield the above named compound.

Example 7H 5-(3-((1S,2R,3R,5R)-5-cyano-2-((E)-4-(1-ethylcyclobutyl)-4-hydroxybut-1-enyl)-3-hydroxycyclopentyl)propyl)thiophene-2-carboxylic acid The faster moving isomer obtained via Example 20 was reacted in accordance with the process of Example 1H to yield the above named compound.

Example 7L 5-(3-((1S,2R,3R,5R)-5-cyano-2-((E)-4-(1-ethylcyclobutyl)-4-hydroxybut-1-enyl)-3-hydroxycyclopentyl)propyl)thiophene-2-carboxylic acid The slower moving isomer obtained via Example 20 was reacted in accordance with the process of Example 1H to yield the above named compound.

Example 8H 5-(3-((1S,2R,3R,5R)-5-cyano-2-(4-(1-ethylcyclobutyl)-4-hydroxybutyl)-3-hydroxycyclopentyl)propyl)thiophene-2-carboxylic acid The compound obtained via Example 7H was reacted in accordance with the process of Example 2H to yield the above named compound.

Example 8L 5-(3-((1S,2R,3R,5R)-5-cyano-2-(4-(1-ethylcyclobutyl)-4-hydroxybutyl)-3-hydroxycyclopentyl)propyl)thiophene-2-carboxylic acid The compound obtained via Example 7L was reacted in accordance with the process of Example 2H to yield the above named compound.

Example 21

(E)-tert-butyl(4-iodo-1-(1-(thiophen-2-yl)cyclobutyl)but-3-enyloxy)dimethylsilane The named compound was purchased from JSTAR RESEARCH, Inc., South Plainfield, N.J., 07080

Example 22

(E)-tert-butyl(1-(1-((5-chlorothiophen-2-yl)methyl)cyclobutyl)-4-iodobut-3-enyloxy)dimethylsilane The compound obtained via Example 23 was reacted in accordance with the process of Example 15 to yield the above named compound.

Example 23 tert-butyl(1-(1-((5-chlorothiophen-2-yl)methyl)cyclobutyl)but-3-ynyloxy)dimethylsilane The named compound was purchased from JSTAR RESEARCH, Inc., South Plainfield, N.J., 07080

Example 3H (Z)-7-((1S,2R,3R,5R)-2-((E)-4-(1-((5-chlorothiophen-2-yl)methyl)cyclobutyl)-4-hydroxybut-1-enyl)-5-cyano-3-hydroxycyclopentyl)hept-5-enoic acid Substituting Vinyl Iodide (22) for Vinyl Iodide (15), the processes described in Examples 9-1H were used to yield the above named compound.

Example 3L (Z)-7-((1S,2R,3R,5R)-2-((E)-4-(1-((5-chlorothiophen-2-yl)methyl)cyclobutyl)-4-hydroxybut-1-enyl)-5-cyano-3-hydroxycyclopentyl)hept-5-enoic acid Substituting Vinyl Iodide (22) for Vinyl Iodide (15), the processes described in Examples 9-1L were used to yield the above named compound.

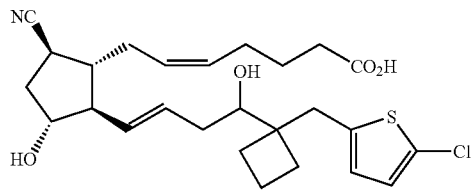

The compound above has the following activity at the EP2 receptor according to the assays described in WO 2005/044501.

cAMP assay: EC50=3 nM
Binding Ki: 116

Treatment of inflammatory bowel disease may be accomplished by the administration of the compounds described herein to the suffering mammal. Inflammatory bowel disease describes a variety of diseases characterized by inflammation of the bowels including, but not limited to, ulcerative colitis and Crohn's disease. Treatment may be accomplished by oral administration, by suppository, or parenteral administration, or some other suitable method.

While not intending to limit the scope of the invention in any way, delivery of the compounds disclosed herein to the colon via oral dosage forms may be accomplished by any of a number of methods known in the art. For example, reviews by Chourasia and Jain in J Pharm Pharmaceut Sci 6 (1): 33-66, 2003 and Shareef et. al (AAPS PharmSci 2003; 5 (2) Article 17) describe a number of useful methods. While not intending to limit the scope of the invention in any way these methods include 1) administration of a prodrug, including an azo or a carbohydrate based prodrug; 2) coating the drug with, or encapsulating or impregnating the drug into a polymer designed for delivery to the colon, 3) time released delivery of the drug, 4) use of a bioadhesive system; and the like.

While not intending to be bound in any way by theory, it is believed that intestinal microflora are capable of reductive cleavage of an azo bond leaving the two nitrogen atoms as amine functional groups. While not intending to limit the scope of the invention in any way, the azo prodrug approach has been used to deliver to 5-aminosalicylic acid to the colons of humans in clinical trials for the treatment of inflammatory bowel disease. It is also believed that bacteria of the lower GI also have enzymes which can digest glycosides, glucuronides, cyclodextrins, dextrans, and other carbohydrates, and ester prodrugs formed from these carbohydrates have been shown to deliver the parent active drugs selectively to the colon. For example, in vivo and in vitro studies on rats and guinea pigs with prodrugs of dexamethasone, prednisolone, hydrocortisone, and fludrocortisone, suggest that glycoside conjugates may be useful for the delivery of steroids to the human colon. Other in vivo studies have suggested that glucuronide, cyclodextrin, and dextran prodrugs of steroids or non-steroidal anti-inflammatory drugs are useful for delivery of these drugs to the lower GI tract. An amide of salicylic acid and glutamic acid has been shown to be useful for the delivery of salicylic acid to the colon of rabbit and dog.

While not intending to limit the scope of the invention in any way, carbohydrate polymers such as amylase, arabinogalactan, chitosan, chondroitin sulfate, dextran, guar gum, pectin, xylin, and the like, or azo-group containing polymers can be used to coat a drug compound, or a drug may be impregnated or encapsulated in the polymer. It is believed that after oral administration, the polymers remain stable in the upper GI tract, but are digested by the microflora of the lower GI thus releasing the drug for treatment.

Polymers which are sensitive to pH may also be used since the colon has a higher pH than the upper GI tract. Such polymers are commercially available. For example, Rohm Pharmaceuticals, Darmstadt, Germany, commercially provides pH dependent methacrylate based polymers and copolymers which have varying solubilities over different pH ranges based upon the number of free carboxylate groups in the polymer under the tradename Eudragit®. Several Eudragit® dosage forms are currently used to deliver salsalazine for the treatment of ulcerative colitis and Crohn's disease. Time release systems, bioadhesive systems, and other delivery systems have also been studied.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:
1. A compound having the formula

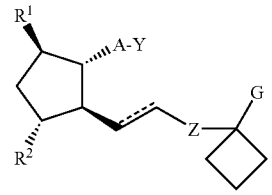

or a pharmaceutically acceptable salt thereof;
wherein Y is an organic acid functional group, or an amide or ester thereof comprising up to 14 carbon atoms; or Y is hydroxymethyl or an ether thereof comprising up to 14 carbon atoms; or Y is a tetrazolyl functional group;
A is —$(CH_2)_6$—, cis-$CH_2CH=CH$—$(CH_2)_3$—, or —$CH_2C\equiv C$—$(CH_2)_3$—, wherein 1 or 2 carbon atoms may be replaced by S or O; or A is —$(CH_2)_m$—Ar—$(CH_2)_o$— wherein Ar is interarylene or heterointerarylene, the sum of m and o is 1, 2, 3, or 4, and wherein one $CH_2$ may be replaced by S or O;
$R^1$ is CN or OH;
$R^2$ is H, CN, OH, F, Cl, Br, or $CH_3$ with the proviso that if $R^1$ is OH, $R^2$ is not OH;
Z is $CH_2CHOH$, $CHOHCH_2$, or CHOH;
G is L, $CH_2L$, OL, or SL;
L is phenyl, monocyclic heteroaryl, or $C_{1-6}$ alkyl.
2. The compound of claim 1 wherein L is thienyl.
3. The compound of claim 2 wherein L is chlorothienyl.
4. The compound of claim 1 wherein $R^1$ is CN.
5. The compound of claim 1 wherein $R^1$ is OH.
6. The compound of claim 1 wherein $R^2$ is OH, H CN, F, Cl, Br or $CH_3$.
7. The compound of claim 1 wherein Z is $CH_2CHOH$, $CHOHCH_2$, or CHOH.

8. The compound of claim 1 wherein Y is $CO_2R^3$, $CON(R^3)_2$, $CON(OR^3)R^3$, $CON(CH_2CH_2OH)_2$, $CONH(CH_2CH_2OH)$, $CH_2OH$, $P(O)(OH)_2$, $CONHSO_2R^3$, $SO_2N(R^3)_2$, $SO_2NHR^3$,

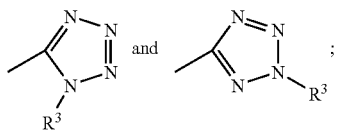

wherein $R^3$ is independently H, $C_1$-$C_6$ alkyl, unsubstituted phenyl, or unsubstituted biphenyl.

9. The compound of claim 1 wherein Y is $CO_2R^3$.

10. The compound of claim 1 wherein G is L, $CH_2L$, OL, or SL.

11. The compound of claim 1 wherein L is phenyl, pyridinyl, or furyl.

12. The compound of claim 1 wherein L is furyl.

13. The compound of claim 1 wherein L is unsubstituted or has 1 or 2 substituents independently selected from F, Cl, OH, $OCH_3$, $CH_3$, $CF_3$, $NO_2$, and CN.

14. The compound of claim 2 wherein $R^1$ is CN.

15. The compound of claim 1 of the formula

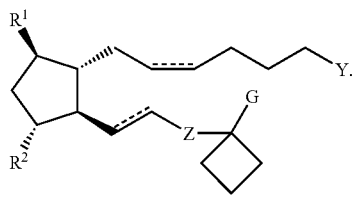

16. The compound of claim 15 of the formula

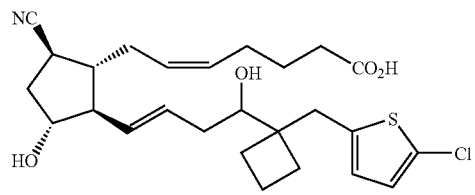

or a pharmaceutically acceptable salt thereof.

17. The compound of claim 1 of the formula

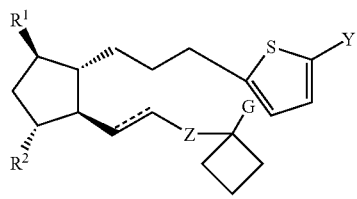

or a pharmaceutically acceptable salt thereof.

18. The compound of claim 1 wherein G is $C_{1-6}$ alkyl.

19. The compound of claim 18 wherein G is ethyl.

20. A composition comprising a compound according to claim 1 wherein the composition is a liquid which is ophthalmically acceptable.

* * * * *